(12) United States Patent
Draganoiu et al.

(10) Patent No.: US 11,969,486 B2
(45) Date of Patent: Apr. 30, 2024

(54) DENTURE ADHESIVES

(71) Applicant: Lubrizol Advanced Materials, Inc., Cleveland, OH (US)

(72) Inventors: Elena S. Draganoiu, Toronto (CA); Antonio Moroni, Morris Plains, NJ (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 93 days.

(21) Appl. No.: 17/665,139

(22) Filed: Feb. 4, 2022

(65) Prior Publication Data

US 2022/0151879 A1 May 19, 2022

Related U.S. Application Data

(63) Continuation of application No. 16/495,441, filed as application No. PCT/US2018/023918 on Mar. 23, 2018, now abandoned.

(60) Provisional application No. 62/475,391, filed on Mar. 23, 2017.

(51) Int. Cl.
*A61K 6/35* (2020.01)
*C08L 1/28* (2006.01)
*C08L 33/02* (2006.01)

(52) U.S. Cl.
CPC ............... *A61K 6/35* (2020.01); *C08L 1/286* (2013.01); *C08L 33/02* (2013.01); *C08L 2203/02* (2013.01); *C08L 2205/03* (2013.01); *C08L 2205/035* (2013.01)

(58) Field of Classification Search
CPC ............ C08L 1/284; C08L 5/04; C08L 33/02
See application file for complete search history.

(56) References Cited

U.S. PATENT DOCUMENTS

| | | | |
|---|---|---|---|
| 2,798,053 A | 7/1957 | Brown | |
| 3,003,988 A | 10/1961 | Germann et al. | |
| 3,915,921 A | 10/1975 | Schlatzer, Jr. | |
| 4,136,163 A | 1/1979 | Watson et al. | |
| 4,267,103 A | 5/1981 | Cohen | |
| 4,459,425 A | 7/1984 | Amano et al. | |
| 4,542,168 A * | 9/1985 | Chang | A61K 6/35 523/118 |
| 4,980,391 A | 12/1990 | Kumar et al. | |
| 5,037,924 A | 8/1991 | Tazi et al. | |
| 5,073,604 A | 12/1991 | Holeva et al. | |
| 5,082,913 A | 1/1992 | Tazi et al. | |
| 5,288,814 A | 2/1994 | Long, II et al. | |
| 5,349,030 A | 9/1994 | Long, II et al. | |
| 5,525,652 A | 6/1996 | Clarke et al. | |
| 5,561,177 A * | 10/1996 | Khaledi | A61K 6/35 524/35 |
| 5,900,470 A | 5/1999 | Prosise et al. | |
| 6,294,594 B1 | 9/2001 | Borja et al. | |
| 6,350,794 B1 * | 2/2002 | Borja | A61K 6/35 523/120 |
| 2015/0313800 A1 * | 11/2015 | Hayag | A61K 6/60 523/120 |
| 2020/0069533 A1 * | 3/2020 | Draganoiu | C08L 5/04 |

OTHER PUBLICATIONS

Carbopol Polymer Excipients (Year: 2021).*
Aqualon CMC 7H3SXF (Year: 2021).*

* cited by examiner

*Primary Examiner* — Peter A Salamon
(74) *Attorney, Agent, or Firm* — Eryn A. Fuhrer; Thoburn T. Dunlap

(57) ABSTRACT

The disclosed technology provides improved adhesive composition of use with dentures. These improved compositions include (a) a cross linked poly(acrylic) acid polymer, in combination with (b) a carbomethylcellulose (CMC) component and/or (c) an adherence promoting component. The compositions balance the many competing goals for effective denture adhesives, including adhesive strength and dispensing viscosity, without the need for zinc.

8 Claims, No Drawings

DENTURE ADHESIVES

CROSS REFERENCE TO RELATED APPLICATION

This application is a continuation application of U.S. Ser. No. 16/495,441 filed on Sep. 19, 2019, which claims priority from PCT/US2018/023918 filed on Mar. 23, 2018, which claims the benefit of Provisional U.S. Ser. No. 62/475,391 filed on Mar. 23, 2017, both of which are incorporated in their entirety by reference herein.

FIELD OF THE INVENTION

The disclosed technology provides improved adhesive composition of use with dentures. These improved compositions include (a) a cross linked poly(acrylic) acid polymer, in combination with (b) a carbomethylcellulose (CMC) component and/or (c) an adherence promoting component. The compositions balance the many competing goals for effective denture adhesives, including adhesive strength and dispensing viscosity, without the need for zinc.

BACKGROUND

Approximately, 37 million people in the United States alone are without their natural teeth (see Mojon P, Thomason J M, Walls A W G. The impact of falling rates of edentulism. Int J Prosthodont 2004; 17: 434-40). As the elderly population is increasing, this number is expected to increase over the foreseeable future. Adding to this, the need of replacing a large number of worn out and defective prostheses will result in an estimated need of at least 61 million of new dentures (see Douglass C W, Shih A, Ostry L. Will there be a need for complete dentures in the United States in 2020? J Prosthet Dent 2002; 87: 5-8). Worldwide, this number is expected to grow much higher as a significantly large number of people in developing countries will live longer and also will become wealthy enough to afford dental prostheses.

Denture adhesive is used by more than 5 million denture wearers in the United States alone (see Young R, Weikel M. An appraisal of denture adhesive powders. Contact Point 1945; 23: 247-9). Use of denture adhesive has become more and more popular in the United States and Europe to improve retention, soothe irritated gums and helps with the use of ill-fitting dentures, especially in patients with severely resorbed residual alveolar ridges (see Grasso J E. Denture Adhesives: changing attitudes. J. Am Dent Assoc 1996; 127:90-6). In fact, denture adhesive reduces the amount of undesirable denture movement in the mouth, promotes retention, increases the occlusal force (see Kapur K K. A clinical evaluation of denture adhesives. J Prosthet Dent 1967; 127: 90-6), promotes faster more complete and natural mastication, and is safe and effective (see Shay K. Denture Adhesives. Choosing the right powders and pastes. J Am Dent Assoc 1991; 122:70-6). Unmet needs for denture adhesives include the desire for quicker adhesion development, higher bite force, cushioning, and all-day retention. Irritation that may lead to inflammation reduction, delivery of pleasant, refreshing taste to the mouth is also desirable, as well as adhesive cost reduction, especially for developing countries.

Denture adhesives work by swelling in the presence of saliva and becoming viscous and sticky as water is absorbed. Materials such as natural gums, such as karaya, tragacanth, acacia, and pectin, and also Polyox and Sodium carboxymethylcellulose (CMC) have been used as adhesives in the past but they have been replaced by longer lasting and more effective synthetic polymers that have been developed primarily for this purpose, and consist of various salts of the maleic anhydride/methyl vinyl ether (MA/MVE) copolymer, generally in combination with other gums such as Na CMC or/and Polyox. In certain cases where very strong hold, lasting several days is desired, adhesives based on poly(vinyl acetate) a.k.a. PVA are used, although these products are very hard to squeeze out of the tube, difficult to remove, and are not benign on the mucosal surfaces.

Modern denture adhesives are available in various physical forms, such as creams, strips, powders, and cushions to fulfill a range of customer preferences. However, dental professionals are most likely to recommend a cream-type denture adhesive and these hold the majority of the market share (see Kororis S, Pizatos E, Polyzois G, Lagouvardos P. Clinical evaluation of three denture cushion adhesives by complete denture wearers. Gerodontology 2012; 29: 161-169; and Adisman I K. The use of denture adhesives as an aid to denture treatment. J Prosthet Dent 1989; 62: 711-715). Denture adhesives contain both active and non-active ingredients; active ingredient that confer adhesion properties include all the materials mentioned above while non-active ingredients are mixtures of petrolatum and mineral oils, used to suspend the gums/polymer particles, facilitate dispensing, aid in correct positioning, and prevent premature adhesion while trying to position the denture. Upon exposure to saliva, the oily component is washed away and the adhesives are activated by hydration, thus developing their adhesion properties.

Considerable effort has been made over the years to develop improved denture adhesive compositions. Both synthetic and natural polymers and gums have been used singly, in combination, and in combination with various adhesives and other materials in an attempt to lessen certain deficiencies. These deficiencies include inadequate holding power and messiness and difficulty of removing the residual adhesive from the mouth and dentures. Also, food may become trapped between the denture and the oral cavity of the wearer. Additionally, certain components may present a less than desirable taste to the wearer.

Alkyl vinyl ether-maleic copolymers and salts thereof are known in the art for use in denture adhesive compositions. Such disclosures include: U.S. Pat. No. 3,003,988 to Germann et al., issued Oct. 10, 1961; U.S. Pat. No. 4,980,391 to Kumar et al., issued Dec. 25, 1990; U.S. Pat. No. 5,073,604 to Holeva et al., issued Dec. 17, 1991; U.S. Pat. No. 5,900,470, Prosise et al., issued May 4, 1999; U.S. Pat. No. 5,037,924, Tazi et al, issued Aug. 6, 1991; U.S. Pat. No. 5,082,913, Tazi et al., issued Jan. 21, 1992; and U.S. Pat. No. 5,525,652 to Clarke, issued Jun. 11, 1996. In addition, strip or insert denture adhesives are also known. Despite the above-noted technologies, as well as many others, a need still exists for improved denture stabilizing compositions.

Adhesive strength and dispensing viscosity are the most important properties of a denture adhesive. An ideal denture adhesive should retain its adhesive properties for 12 to 16 hours before requiring re-application, be quick to develop initial holding power (2-5 minutes with maximum reached in the 2-4 hours timeframe) and be easy to dispense from the tube. Color similar to that of gums, pleasant flavor and, eventually, anti-bacterial, anti-irritation, soothing actions are other beneficial qualities that a denture adhesive may have.

There is a need for improved denture adhesive compositions that balance these needs and provide good performance across all of these areas.

SUMMARY

The disclosed technology provides improved denture adhesive compositions, methods of making such compositions and methods of using the same.

The disclosed technology provides a denture adhesive composition comprising: (a) a cross-linked poly(acrylic) acid polymer and (b) and additional component, comprising (i) a carboxymethylcellulose (CMC) component, (ii) an adherence promoting component, or (iii) both (i) and (ii). The compositions may also include one or more other components and/or additives know in field for use in such compositions. In some embodiments, the compositions further include petrolatum, mineral oil, or both.

The cross-linked poly(acrylic) acid polymer may be present in the overall composition from about 9 to about 27 percent by weight, or even from 10 to 20, 10 to 14, or even about 12 percent by weight.

The carboxymethylcellulose component may be present in the overall composition from about 0 to about 43 percent by weight, about 20 to about 43 percent by weight, or even from 20 to 41 or from 20 to 30, or from 20 to 25, or from 20 to 21, or even about 20.5 percent by weight.

The adherence promoting component may include sodium alginate, poly(ethylene) oxide, or a combination thereof. In some embodiments, the adherence promoting component is sodium alginate. In some embodiments, the adherence promoting component is poly(ethylene) oxide.

The adherence promoting component may be present in the overall composition from about 20 to about 42 percent by weight, or even from 15 to 25, or from 18 to 22, or even about 20 percent by weight, or even from 35 to 45 or from 36 to 44, or from 40 to 42 or even about 41 percent by weight.

When present, the mineral oil may be present at various levels, however in some embodiments mineral oil may be present in the overall composition from about 20 to about 40 percent by weight, or even from 25 to 35, or from 30 to 34, or even about 32 percent by weight.

When present, the petrolatum may be present at various levels, however in some embodiments petrolatum may be present in the overall composition from about 10 to about 20 percent by weight, or even from 12 to 16, or from 13 to 15, or even about 14 percent by weight.

Further, in some embodiments, it has been found that where the weight ratio of component (b) to component (a) is from 5:1 to 1:5, or from 4:1 to 1:4, or even 4:1 to 1:1, or from 2:1 to 1:1.

The disclosed technology further provides the described denture adhesive where the cross-linked poly(acrylic) acid polymer is a carbomer homopolymer, carbomer copolymer, carbomer interpolymer, polycarbophil or a mixture thereof.

The disclosed technology further provides the described denture adhesive where the cross-linked poly(acrylic) acid polymer is a homopolymer, a copolymer, or an interpolymer.

The disclosed technology further provides the described denture adhesive where the cross-linked poly(acrylic) acid polymer includes Carbopol® 971P NF, Carbopol® 974P NF, Carbopol Ultrez 10NF, Carbopol ETD 2020NF, Carbopol 980NF, Pemulen TR-1 or TR-2 NF or any combination thereof.

The disclosed technology further provides the described denture adhesive where the cross-linked poly(acrylic) acid polymer includes Carbopol® 974P NF.

The disclosed technology further provides the described denture adhesive where the carboxymethylcellulose component includes a sodium carboxymethylcellulose.

The disclosed technology further provides the described denture adhesive where the carboxymethylcellulose component includes a carboxymethylcellulose with seven degrees of substitution, a high viscosity grade, a viscosity of about 3000 cps viscosity, a smooth flow property, a fine particle size, and made to at least a food grade standard.

The disclosed technology further provides the described denture adhesive where the carboxymethylcellulose component includes Aqualon™ 7H3 SF, Aqualon™ 7HF, Aqualon™ 7MF, Aqualon™ 9M31XF, Aqualon™ CMC 9M8F PH, or any combination thereof.

The disclosed technology further provides the described denture adhesive where adherence promoting component includes sodium alginate.

The disclosed technology further provides the described denture adhesive where adherence promoting component includes poly(ethylene) oxide.

The disclosed technology further provides the described denture adhesive where the composition further includes a medium, where said medium includes a mineral oil, petrolatum, or a mixture thereof.

The disclosed technology further provides the described denture adhesive where the composition further includes a medium, where said medium includes a mineral oil, petrolatum, or a mixture thereof, and wherein the medium is present in an amount from about 14 to about 50 percent by weight.

The disclosed technology further provides the described denture adhesive where the composition includes components (a), (b)(i), and (b)(ii), where the cross-linked poly(acrylic) acid polymer of (a) includes Carbopol® 971P NF; the carboxymethylcellulose component of (b)(i) includes a sodium carboxymethylcellulose; where the adherence promoting component of (b)(ii) includes sodium alginate; and where the composition further includes a mineral oil, petrolatum, or a mixture thereof.

The disclosed technology further provides the described denture adhesive where the composition includes components (a) and (b)(ii); where said cross-linked poly(acrylic) acid polymer of (a) includes Carbopol® 971P NF; where the adherence promoting component of (b)(ii) includes poly(ethylene) oxide; and where the composition further includes a mineral oil, petrolatum, or a mixture thereof.

The disclosed technology further provides the described denture adhesive where the cross-linked poly(acrylic) acid polymer includes Carbopol® 971P NF, Carbopol® 974P NF, Carbopol Ultrez 10NF, Carbopol ETD 2020NF, Carbopol 980NF, Pemulen TR-1 or TR-2 NF or any combination thereof; the carboxymethylcellulose component includes a sodium carboxymethylcellulose; and the composition further includes a mineral oil, petrolatum, or a mixture thereof.

The disclosed technology further provides the described denture adhesive where the cross-linked poly(acrylic) acid polymer includes Carbopol® 974P NF at about 10 to about 14 percent by weight; the carboxymethylcellulose component includes a sodium carboxymethylcellulose present at about 0 to about 24 percent by weight; the adherence promoting component includes sodium alginate or poly(ethylene) oxide and is present at about 18 to about 45 percent by weight; the composition further includes a mineral oil present at about 30 to about 34 percent by weight; and the composition further includes petrolatum present at about 12 to about 16 percent by weight.

The disclosed technology further provides the described denture adhesive where the cross-linked poly(acrylic) acid polymer includes Carbopol® 971P NF, Carbopol® 71G NF, Carbopol® 974P NF, or any combination thereof; the carboxymethylcellulose component includes a sodium carboxymethylcellulose; and the composition further includes a mineral oil, petrolatum, or a mixture thereof.

The disclosed technology further provides the described denture adhesive where the cross-linked poly(acrylic) acid polymer includes Carbopol® 974P NF at about 10 to about 14 percent by weight; the carboxymethylcellulose component includes a sodium carboxymethylcellulose present at about 18 to about 24 percent by weight; the adherence promoting component includes sodium alginate or poly (ethylene) oxide and is present at about 18 to about 45 percent by weight; the composition further includes a mineral oil present at about 30 to about 34 percent by weight; and the composition further includes petrolatum present at about 12 to about 16 percent by weight.

The disclosed technology further provides the described denture adhesive where the composition is free of alkyl vinyl ether-maleic copolymers and salts thereof. The disclosed technology further provides the described denture adhesive where the composition is free of zinc. The disclosed technology further provides the described denture adhesive where the composition is free of alkyl vinyl ether-maleic copolymers and salts thereof and is also free of zinc.

DETAILED DESCRIPTION

Various preferred features and embodiments will be described below by way of non-limiting illustration.

The disclosed technology provides improved denture adhesive compositions, methods of making such compositions and methods of using the same.

The Cross-Linked Poly(Acrylic) Acid Polymer

The drug compositions disclosed herein include a cross-linked poly(acrylic) acid polymer. The cross-linked polyacrylic acid polymer can be a carbomer homopolymer, carbomer copolymer, carbomer interpolymer, polycarbophil or a mixture thereof.

The cross-linked polyacrylic acid may be selected from one or more carbomers, one or more polycarbophils, one or more copolymers of acrylic acid and alkyl acrylates, or combinations of two or more thereof.

As used herein, the term polyacrylic acid or acrylic acid polymers is used to encompass a variety of polymers having high percentages of polymerizable monomers therein with pendant carboxylic acid groups or anhydrides of polycarboxylic acid. These compounds are described in more detail in U.S. Pat. Nos. 2,798,053; 3,915,921; 4,267,103; 5,288,814; and 5,349,030, all of which are hereby incorporated by reference in their entireties. The term polyacrylic acid is also used to include various homopolymers, copolymers, and interpolymers, wherein at least 50 or 75 mole percent of the repeating units have pendant carboxylic acid groups or anhydrides of dicarboxylic acid groups. While acrylic acid is the most common primary monomer used to form polyacrylic acid the term is not limited thereto but includes generally all alpha-beta-unsaturated monomers with carboxylic pendant groups or anhydrides of dicarboxylic acids as described in U.S. Pat. No. 5,349,030.

Suitable cross-linked polyacrylic acids include, but are not limited to polycarbophils, carbomers, Carbopol® polymers, Carbopol homopolymers, Carbopol copolymers, Carbopol interpolymers copolymers of acrylic acid and alkyl acrylates, or combinations of two or more thereof. An approved polyacrylic acid for pharmaceutical applications, described in a carbomer monograph in the U.S.P. Pharmacopeia 30 NF 25, is a polyacrylic acid crosslinked with polyalkenyl ethers.

In some embodiments, the poly(acrylic) acid polymer used in the described compositions is cross-linked by an allyl ether cross-linking agent, divinyl glycol, or a combination thereof. In some embodiments, the poly(acrylic) acid polymer used in the described compositions is cross-linked by an allyl ether cross-linking agent. In some embodiments, the poly(acrylic) acid polymer used in the described compositions is cross-linked by divinyl glycol In some embodiments, the cross-linked poly(acrylic) acid polymer includes Carbopol 971P NF, Carbopol 974P NF, Carbopol Ultrez 10NF, Carbopol ETD 2020NF, Carbopol 980NF, Pemulen TR-1 or TR-2 NF or any combination thereof. In some embodiments, the cross-linked poly (acrylic) acid polymer includes Carbopol 974P NF.

The Carboxymethylcellulose Component

The compositions herein contain from about 0 to about 43 percent by weight, or from about 20 to about 43 percent by weight, or even from 10, 15, 17, or even 20 percent by weight up to 43, 41, 30, 25, 21, or even 20 percent by weight of the adhesive composition, of carboxymethylcellulose.

In one embodiment, the carboxymethylcellulose is sodium carboxymethylcellulose. Carboxymethylcellulose materials useful herein include those having a molecular weight of at least 200,000 daltons. In some embodiments, the carboxymethylcellulose has a molecular weight of from about 200,000 to about 1,000,000, alternatively from about 500,000 to 900,000, or from about 600,000 to about 800,000 daltons. Examples of commercially available carboxymethylcelluloses useful herein include the 7H series of carboxymethylcelluloses available from Aqualon having a typical molecular weight of about 700,000 daltons per their brochure materials. Other examples of useful carboxymethylcellulose include 7H3 SX8F and 7H3 SXF both commercially available from Aqualon/Hercules and CEKOL 30,000P from C. P. Kelco/Noviant/Huber.

In some embodiments, the carboxymethylcelluloses used in the described compositions is 7H3SXF.

The Adherence Promoting Component.

The compositions of the invention include an adherence promoting component. The adherence promoting component may be sodium alginate, poly(ethylene) oxide, or a combination thereof. In some embodiments, the adherence promoting component is sodium alginate. In some embodiments, the adherence promoting component is poly(ethylene) oxide.

Sodium alginate is a polysaccharide commercially available from FMC BioPolymer. Poly(ethylene) oxide is available from various commercial sources, including Dow Chemical under the brand Polyox™.

Poly(ethylene) oxide or polyoxyethylene (POE), is a polyether compound with many applications from industrial manufacturing to medicine and used as an excipient in many pharmaceutical products. Lower-molecular-weight variants are used as solvents in oral liquids and soft capsules, whereas solid variants are used as ointment bases, tablet binders, film coatings, and lubricants, including lubricating eye drops. POE (W 301 grade) has been used as a main adhesion promoter in legacy denture adhesive formulation because of it stickiness, although lacking cohesive strength. Nowadays, POE is still used as a co-adhesive in some modern denture adhesive formulations where it acts synergistically with other materials. Combination of POE with the cross-linked poly(acrylic) acid polymers described herein is believed to bring about some of the benefits of the described compositions.

Alginic acid, also called algin or alginate, is an anionic polysaccharide distributed widely in the cell walls of brown algae, where through binding with water it forms a viscous gum. In extracted form it absorbs water quickly and it is capable of absorbing 200-300 times its own weight in water. Often, alginic acid is converted into the raw material commonly known as sodium alginate, a material that has a wide use across a wide variety of industries including food, textile printing and pharmaceutical. Dental impression material utilizes alginate as its means of gelling. Alginate is both food and skin safe. Combination of sodium alginate with the cross-linked poly(acrylic) acid polymers described herein is believed to bring about some of the benefits of the described compositions.

The adherence promoting component may be present in the overall composition from about 20 to about 42 percent by weight, or even from 15 to 25, or from 18 to 22, or even about 20 percent by weight, or even from 35 to 45 or from 36 to 44, or from 40 to 42 or even about 41 percent by weight.

Additional Additives and Components

The disclosed compositions may include one or more additional components and/or additives.

In some embodiments the disclosed compositions include a carrier. The carrier may be present at various levels, but in some embodiments the described compositions include from about 2% to about 80%, or from about 30% to about 70%, of a carrier such as a water-insoluble liquid, gel, thermoplastic solid, or combinations thereof.

In general, water-insoluble blends of mineral oil and petrolatum may be used as a carrier to make the composition into a suspension. This suspension of solid-particles in a liquid/gel vehicle/carrier is also referred to as a denture adhesive cream or paste. In some embodiments, the present composition comprises a safe and effective amount of a water insoluble component (wic). In one embodiment, this component is present by weight of the composition in an amount from about 2, 5, 10, 20, 25, 30, 35% to about 45, 50, 60, 70, 90%, or any combination thereof. In additional embodiments, the water insoluble component is present at an amount from about 20% to about 70%, from about 25% to about 60%, or from about 35% to about 60% by weight of the composition. In yet another embodiment, the water insoluble component is substantially non-swellable in water. In some embodiments, the non-swellable water insoluble component swells less than about 10%, 5%, 2%, or 1% in water.

In one embodiment, the water insoluble component comprises a liquid, gel, or mixtures thereof. In one embodiment, the water insoluble component is selected from the group consisting of: natural wax, synthetic wax, petrolatum, polyvinyl acetate, natural oils, synthetic oils, fats, silicone, silicone derivatives, dimethicone, silicone resins, hydrocarbons, hydrocarbon derivatives, essential oils, caprylic/capric triglycerides, polybutene, oleic acid, stearic acid, and combinations thereof. In a further embodiment, the water insoluble component comprises petrolatum, polyvinyl acetate, natural oils, synthetic oils, fats, silicone, silicone derivatives, dimethicone, silicone resins, hydrocarbons, hydrocarbon derivatives, polybutene, oleic acid, stearic acid, essential oils, or combinations thereof.

Examples of natural oils include, but are not limited to, vegetable oils (ex. corn oil), soy bean oils, cottonseed oils, palm oils, coconut oils, mineral oils, animal oils (ex. fish oils), etc. Examples of synthetic oils include, but are not limited to, silicone oils, etc. In one embodiment, the water insoluble component comprises a natural oil. In an additional embodiment, the water insoluble component is substantially free of petrolatum. In another embodiment, the water insoluble component further comprises petrolatum. In other embodiments, the water insoluble component may comprise mineral jelly, for example, mineral jellies numbers 4, 5, 10, 15, or 20 from Calumet Specialty Products.

In a further embodiment, the natural oil comprises mineral oil. In one embodiment, mineral oil is present in the composition at an amount from about 30% to about 50% and in another embodiment, from about 35% to about 45%. In some embodiments, the mineral oil may be white, light, or technical. Light mineral oil may be, for example, Drakeol 5, 10, 13, or 15. White mineral oil may be, for example, Drakeol 19, 21, 34, 35, or 600.

In some embodiments, the water insoluble component comprises a wax. Waxes are generally made up of various substances including hydrocarbons (normal or branched alkanes and alkenes), ketones, diketones, primary and secondary alcohols, aldehydes, sterol esters, alkanoic acids, terpenes (squalene) and monoesters (wax esters). Different types of waxes include animal and insect waxes (beeswax, Chinese wax, shellac wax, spermaceti, lanolin), vegetable waxes (bayberry wax, candelilla wax, carnauba wax, castor wax, esparto wax, Japan wax, jojoba oil, ouricury wax, rice bran wax), mineral waxes (cresin waxes, montan wax, ozocerite, peat waxes), petroleum waxes (paraffin wax or microcrystalline wax), and synthetic waxes (polyethylene waxes, Fischer-Tropsch waxes, chemically modified waxes, substituted amide waxes, polymerized .alpha.-olefins).

In one embodiment, the water insoluble component comprises a natural or synthetic wax. In a further embodiment, the natural wax is selected from the group consisting of: animal wax, vegetable wax, mineral wax, and combinations thereof. In another embodiment, the animal wax includes beeswax, lanolin, shellac wax, Chinese wax, and combinations thereof. In another embodiment, the vegetable waxes include carnauba, candelilla, bayberry, sugar cane, and combinations thereof and mineral waxes include fossil or earth waxes (ozocerite, ceresin, montan), and petroleum waxes such as paraffin and microcrystalline wax, and combinations thereof. In one embodiment, the waxes herein are natural waxes selected from the group consisting of beeswax, candelilla, candela, carnauba, paraffin, and combinations thereof. In varying embodiments, wax can be present in an amount from about 1, 2, 5, 8% to about 5, 10, 20, 30%, or any combination thereof.

In another embodiment, the natural wax comprises paraffin wax. A paraffin wax useful herein generally can have a melting point range of from about 65° C. to about 80° C. and, in another embodiment, from about 70° C. to about 75° C. In another embodiment, a microcrystalline wax useful herein can have a melting point of from about 65° C. to about 90° C., and, in another embodiment from about 80° C. to about 90° C. In one embodiment, a beeswax useful herein can have a melting point of from about 62° C. to about 65° C. and a flash point of 242° C. In another embodiment, a candelilla wax useful herein can have a melting point of from about 68° C. to about 72° C. In an additional embodiment, a carnauba wax useful herein can have a melting point of from about 83° C. to about 86° C. In one embodiment, a Fischer-Tropsch wax useful herein can have a melting point of about 95° C. to about 120° C. Synthetic grades of beeswax, candelilla, and carnauba waxes are also available with similar properties as the natural grades.

In one embodiment, the water insoluble component comprises petrolatum. According to Hawley's Condensed Chemical Dictionary 13$^{th}$ Edition, John Wiley & Sons, 1997, petrolatum is a "mixture of hydrocarbons derived by distillation of paraffin-base petroleum fractions"; and according to The United States Pharmacopia 2005, petrolatum is a "purified mixture of semisolid hydrocarbons obtained from petroleum". This is also referred to as "natural petrolatum". Petrolatum is stated to have a melting range between 38° C. and 60° C. according to The United States Pharmacopia 2005, and 38-54 C according to The Merck Index, 10$^{th}$ Edition, 1983. Petrolatums are available in a variety of grades with the "Cone Penetration Values" ranging from 180 to about 245 measured using ASTM D-937 according to the Sonneborn Inc product brochure.

In one embodiment, the water insoluble component has a melting point greater than about 60° C. In some embodiments, the water insoluble thermoplastic component has a melting point from about 35° C., 40° C., 45° C., 50° C., 55° C., 60° C., 65° C., 70° C., 75° C., 80° C., 85° C., 90° C., 95° C., 100° C., to about 110° C., 120° C., 150° C., 175° C., 200° C. and/or any combination thereof to form a range, starting point, and/or end point. In another embodiment, the composition is substantially free of a water insoluble thermoplastic component with a melting point above about 75° C.

In some embodiments, the carrier comprises microcrystalline wax. The microcrystalline wax may be refined and/or substantially pure. In an additional embodiment, petrolatum does not contribute the microcrystalline wax. The "Encyclopedia of Polymer Science and Engineering", 2$^{nd}$ Edition, Vol. 17, page 788, hereby incorporated by reference, states that the molecular weight of microcrystalline wax ranges from 450 to 800. The "Kirk-Othmer Encyclopedia of Chemical Technology", 5$^{th}$ Edition, vol. 26, page 216, hereby incorporated by reference, states that microcrystalline wax has the following typical properties: flash point, closed cup, 260° C.; viscosity at 98.9° C., 10.2-25 mm$^2$/s; melting range, 60° C.-93° C.; refractive index at 98.9° C., 1.435 to 1.445; average molecular weight, 600 to 800; carbon atom per molecule, 30 to 75; and ductibility/crystallinity of solid wax, ductile-plastic to tough-brittle, and in one embodiment, the viscosity index improver has these particular properties.

In another embodiment, the microcrystalline wax has a melting point ranging from about 50° C. to about 100° C. In further embodiments, the microcrystalline wax has a melting point ranging from about 50° C., 55° C., 60° C., 65° C., 70° C. to about 70° C., 75° C., 80° C., 85° C., 90° C., 95° C., 100° C., or any combination thereof. In one particular embodiment, the microcrystalline wax has a melting point ranging from about 75° C. to about 85° C.

In another embodiment, the microcrystalline wax is manufactured by Crompton, Sonneborn (Witco) and referred to and sold under the trademark Mutiwax.RTM.W-835. This wax has a melting point ranging from about 73.9° C. to about 79.4° C. (measured using ASTM D-127), has a penetration at 25° C. of from about 60 to about 80 (measured using ASTM D-1321), has a kinematic viscosity at 98.9° C. of from about 75 to about 90 saybolt universal seconds (measured using ASTM D-2161), has a flash point, COC (Cleveland open cup), of at least about 246° C. (measured using ASTM D-92), and has a congealing point from about 68° C. to about 77° C. (measured using ASTM D-938).

In another embodiment, the microcrystalline wax is manufactured by Crompton, Sonneborn (Witco) and referred to and sold under the trademark Mutiwax® 180W. This wax has a melting point ranging from about 79° C. to about 87° C. (measured using ASTM D-127), has a penetration at 25° C. of from about 15 to about 22 (measured using ASTM D-1321), has a kinematic viscosity at 98.9° C. of at least about 75 saybolt universal seconds (measured using ASTM D-2161), has a flash point, COC (Cleveland open cup), of at least about 277° C. (measured using ASTM D-92), and has a congealing point from about 75° C. to about 82° C. (measured using ASTM D-938).

In another embodiment, the microcrystalline wax is manufactured by Crompton, Sonneborn (Witco) and referred to and sold under the trademark Mutiwax® W445. This wax has a melting point ranging from about 77° C. to about 82° C. (measured using ASTM D-127), has a penetration at 25° C. of from about 25 to about 35 (measured using ASTM D-1321), has a kinematic viscosity at 98.9° C. of from about 75 to about 90 saybolt universal seconds (measured using ASTM D-2161), has a flash point, COC (Cleveland open cup), of at least about 277° C. (measured using ASTM D-92), and has a congealing point from about 72° C. to about 77° C. (measured using ASTM D-938).

While microcrystalline wax and paraffin wax are both petroleum waxes, there are specific differences between them. Microcrystalline wax is a refined mixture of solid, saturated aliphatic hydrocarbons produced by de-oiling certain fractions from the petroleum refining process. In contrast to the more familiar paraffin wax which contains mostly unbranched alkanes, microcrystalline wax contains a higher percentage of isoparaffinic (branched) hydrocarbons and naphthenic hydrocarbons. It is characterized by the fineness of its crystals in contrast to the larger crystal of paraffin wax. It consists of high molecular weight saturated aliphatic hydrocarbons. It is generally darker, more viscous, denser, tackier and more elastic than paraffin waxes, and has a higher molecular weight and melting point. The elastic and adhesive characteristics of microcrystalline waxes are related to the non-straight chain components which they contain. Typical microcrystalline wax crystal structure is small and thin, making them more flexible than paraffin wax.

According to the "Encyclopedia of Polymer Science and Engineering" Volume 17 page 788, 1989 John Wiley & Sons): The molecular weights of paraffin waxes range from about 280 to 560 (C20 to C40); the molecular weights of microcrystalline wax range from 450 to 800 (C35 to C60). The amount of n-alkanes in paraffin wax usually exceeds 75% and can be as high as 100%; microcrystalline waxes are composed predominantly of iso-paraffinic and napthenic saturated hydrocarbons along with some n-alkanes.

According to Kirk-Othmer Encyclopedia of Chemical Technology, John Wiley & Sons, 2005: Paraffin Waxes have a number average molecular weight of 350-420 and carbons per molecule of 20-36; and Microcrystalline waxes have a number average molecular weight of 600-800 and carbons per molecule of 30-75. Paraffin wax is macrocrystalline, brittle, and is composed of 40-90% normal alkanes, with the remainder C18-C36 isoalkanes and cycloalkanes. A paraffin wax is a petroleum wax consisting principally of normal alkanes. Microcrystalline wax is a petroleum wax containing substantial proportions of branched and cyclic saturated hydrocarbons, in addition to normal alkanes. A classification system based on the refractive index of the wax and its congealing point as determined by ASTM D-938 has been developed. Paraffin waxes have a refractive index at 98.9° C. of 1.430-1.433; and microcrystalline waxes have a refractive index at 98.9° C. of 1.435-1.445. Paraffin waxes are friable to crystalline; microcrystalline waxes are ductile-plastic to tough-brittle. Paraffin wax has little affinity for oil; microcrystalline wax has great affinity for oil. Unlike paraffin wax, oil is held tightly in the crystal lattice of the microcrystalline wax, and does not migrate to the surface. Paraffin wax is stated to have a melting point of about 47-65° C., according to Hawley's Condensed Chemical Dictionary 13$^{th}$ Edition, John Wiley & Sons, 1997, and 46-68° C., according to Kirk-Othmer Encyclopedia of Chemical Technology, John Wiley & Sons, 2005. Microcrystalline wax is stated to have a melting point of about 63-88° C., according to Hawley's Condensed Chemical Dictionary 13$^{th}$ Edition, John Wiley & Sons, and 60-93° C., according to according to Kirk-Othmer Encyclopedia of Chemical Technology, John Wiley & Sons, 2005.

In some embodiments, the water insoluble thermoplastic and/or viscosity index improver used in the present invention have a Penetration Value from about 5, 10, 15, 20, 25, 30, 35, 40, 45, 50, 55, 60 to about, 25, 30, 35, 40, 45, 50, 55, 60, 65, 70, 75, 80, 85, 90, 95, 100, 110, 120, 250, in any combination of numbers to form ranges (where the amounts about are in units of ¹⁄₁₀ mm).

In some embodiments, the water insoluble thermoplastic component and/or viscosity index improver such as microcrystalline wax has an average molecular weight higher than that of petrolatum. In some embodiments the water-insoluble component and/or viscosity index improver is higher in MW, more branched, more flexible, stronger, tougher, higher melting, and/or more crystalline than blends of mineral oil combined with petrolatum.

In some embodiments, the described compositions may also include a non-adhesive self-supporting layer.

The disclosed compositions optionally include at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polyurethane, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Some embodiments may comprise non-adhesive cellulose derivatives, polyester, polypropylene, nylon, rayon, cloth, paper, microcrystalline wax, or mixtures thereof. Some embodiments may comprise polyester, polypropylene, rayon, nylon, cloth, and/or paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

The described compositions may also include one or more other adhesive components. These adhesive components, if present, are used in a safe and effective adhesive amount. In general, the other adhesive components may be present at a level of any combination of the ranges from about 0%, 10%, 20%, 30, or 40% to about 50%, 60%, 70%, 80%, or 90%, by weight of the composition.

Suitable adhesive components include a water-soluble hydrophilic colloid or polymer having the property of swelling upon exposure to moisture to form a mucilaginous mass. Such adhesive materials include natural gums, synthetic polymeric gums, alkyl vinyl ether-maleic acid (AVE/MA) copolymer acid, AVE/MA copolymer anhydride, alkyl vinyl ether-maleic acid-isobutylene (AVE/MA/IB), synthetic polymers, mucoadhesive polymers, hydrophilic polymers, saccharide derivatives, other cellulose derivatives, and adhesive materials commonly employed in denture stabilizing compositions and compatible with the subject polymers of the present invention, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyamines, polyquarternary compounds, polybutenes, silicones, ethylene oxide polymers, polyvinylpyrrolidone, cationic polyacrylamide polymers.

In some embodiments, such materials may be other cellulose derivatives, polyethylene glycol, polyethylene oxide, karaya gum, sodium alginate, chitosan, polyvinyl alcohol, or mixtures thereof. In other embodiments, the materials may be other cellulose derivatives such as methylcellulose, hydroxyethylcellulose, hydroxypropylcellulose, hydroxypropylmethylcellulose, or mixtures thereof.

In other embodiments, the compositions of the invention are free of any other adhesive components other than those described in the sections above.

The described compositions may also include one or more additional ingredients.

For example, in some embodiments where the composition includes a non-adhesive self-supporting layer, the layer may also comprise a coating which is sticky to dry dentures and, if present, will be placed on one side of the denture adhesive composition. Compositions suitable for use as this type of adhesive layer include polybutenes, silicones, rubbers, petrolatum, natural polymers, synthetic polymers, and mixtures thereof. The adhesive layer may be present at a level of from about 0% to about 70%, in some embodiments from about 0.5% to about 20%, by weight of the composition.

Other suitable ingredients may include colorants, preservatives such as methyl and propyl parabens; thickeners such as silicon dioxide, and polyethylene glycol; and vehicles such as liquid petrolatum, petrolatum, mineral oil and glycerin. In some embodiments, polyethylene glycol, silicon dioxide, and/or petrolatum may be included. Colorants, preservatives, thickeners and vehicles may be present at levels of from about 0% to about 20%, by weight of the composition.

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants.

The coolant can be any of a wide variety of materials. Included among such materials are carboxamides, menthol, ketals, diols, and mixtures thereof. In some embodiments, coolants in the present compositions may be the paramenthan carboxyamide agents such as N-ethyl-p-menthan-3-carboxamide, known commercially as "WS-3", N-2,3-trimethyl-2-isopropylbutanamide, known as "WS-23," and mixtures thereof. Additional coolants may be selected from the group consisting of menthol, 3-1-menthoxypropane-1, 2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979. These agents may be present at a level of from about 0% to about 50%, by weight of the composition.

Uses and Applications.

The compositions described herein may be used as a denture adhesive and/or used as a bioadhesive on wet tissue such as mucosal tissues, wounds, oral mucosa, etc. The present adhesive compositions can be used to deliver one or more therapeutic actives suitable for topical administration to mucosal or wet tissues. The phrase "therapeutic actives", as used herein, describes agents which are pharmacologically active when absorbed through wet tissue or mucosal surfaces of the body such as the oral cavity, wounds, or applied to the surfaces of the skin. Therapeutic actives may be present at a level of from about 0% to about 70%, by weight of the composition.

Therapeutic actives that are useful in the present compositions may include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, flavors, fragrances, or sensates (warming or cooling agents), and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

The amount of each chemical component described is presented exclusive of any solvent which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions can migrate to other acidic or anionic sites of other molecules. The products formed thereby, including the products formed upon employing the composition of the technology described herein in its intended use, may not be susceptible of easy description. Nevertheless, all such modifications and reaction products are included within the scope of the technology described herein; the technology described herein encompasses the composition prepared by admixing the components described above.

EXAMPLES

The technology described herein may be better understood with reference to the following non-limiting examples.

A series of denture adhesive compositions are prepared and tested. The denture adhesive composition examples are prepared using the following procedure show in Table 1.

TABLE 1

Procedure for Preparing Example

| STEP | INSTRUCTIONS | EQUIPMENT |
|---|---|---|
| 1 | Weight out Petrolatum and Mineral oil and put together into a Hobart mixing vessel set on an electric heating mantle. Batches of size between 500 and 1000 g can be made. | Hobart Mixer |
| 2 | Set temperature of heating mantle under Hobart mixer to allow mineral oil and petrolatum to heat to ~80° C. while slowly mixing to prevent splashing. | Heating mantle, Variac controller and Hobart Mixer |
| 3 | Weigh out Carbomer, CMC and other materials and place them in zipper top plastic bag to mix them together. The mixture is then slowly introduced into the vessel of petrolatum and mineral oil while mixing. | 10 mg resolution balance, I L plastic bag |
| 4 | Once all powder is introduced from stage 3, allow mixing under constant heat (~70-80° C.) for 30 minutes. Stop mixing, remove heat, and then take out denture adhesive, place into 2-4 plastic containers of 250 ml size. Place the capped containers into Humidity chamber at 25° C. | Humidity Chamber 25° C. |
| 5 | After at least 24 hours take out jars and measure viscosity. Use a Brookfield DV-I+ viscometer equipped with Helipath attachment, F spindle, set at 2.5 rpm, cPs reading. Record four viscosity readings taken 10 sec. apart and average. | Brookfield Viscometer DV-I + with Helipath attachment |
| 6 | Place one jar in Humidity chamber at 25° C. and a second jar place in Humidity chamber at 40° C. to observe for phase separation. To quantitate separation, perform analysis using a Turbiscan instrument on samples aged at 40° C. for at least 14 days. | Humidity chamber 25° C. and 40° C Turbiscan instrument |
| 7 | Perform adhesion profile testing saline buffer at 37° C. hydration medium using Instron Electropuls E1000 dynamic mechanical tester equipped with 50 mm stainless steel flat plates and movable hydration chamber. | Instron Electropuls E1000 equipped with movable hydration chamber |

The denture adhesive composition examples are tested using the following test methods.

Separation stability testing, both visual and measured using Turbiscan instrument. Denture adhesive samples are put into scintillation vials to fill these about ¾ of the way up, in a uniform way, avoiding bubbles and making sure that the top surface is flat. Vials are stored in an oven at a constant 40° C. temperature. Oil layer formation at the top should be measured at time intervals for at least 15 days, possibly 21 days, or longer if warranted. Oil layer should be no more that 1 mm, ideally with 1-3 mm borderline acceptable; oil layer thickness of more than 3 mm are not acceptable. Conversely, separation rate as measured by fitting periodic layer thickness measurement with a line should be lower than 0.04 mm/day.

Vibro adhesion adhesive (tensile) strength test as developed at Lubrizol, (derived from 15, 16, 17, and 18). This test is quite new and can supersede tests 4-6. It is performed using an Instron machine equipped with a special fixture consisting of two Stainless Steel, or Lucitone 199 acrylic resin, commonly used to manufacture dentures, plates submersed in a pH 7 saline phosphate buffer: (a) A known amount of denture adhesive is put between the plates, generally 0.2 ml using a 1 ml syringe; (b) The adhesive is hydrated by lifting the water bath to cover the adhesive; (c) The top plate is lowered to touch the top of the adhesive; (d) The machine is balanced; (e) The test is started; plates are compressed up to a defined force, then vibrated for at least 5 cycles at 1 Hz, with a maximum load, to simulate chewing, then allowed to rest for 5 minutes; (f) Plates are compressed to the defined force again, then pulled apart; separation force is measured; (g) Cycles are repeated for up to 1.5 hours or till adhesion force drops below 10 N; (h) Data obtained (at least triplicate) can be averaged and then plotted to generate a curve that shows how adhesion force builds up, reaches a maximum and then fades away.

In addition to the compositions prepared, severally commercially available denture adhesives are included for comparison purposes. These commercial comparative examples are summarized in the table below along with the separation stability measured on each sample using the test procedure above after 14 days. The adhesion force was also tested with the peak adhesion force reported below.

TABLE 2

Commercial Comparative Examples

| Ex No | Active Ingredients | Separation Stability - Layer Height | Peak Adhesion Force (N) |
|---|---|---|---|
| C1 | Polyox, Cellulose Gum | 6.67 mm | 168 |
| C2 | Na, Ca MVE/MA salt; Na CMC | 4.56 mm | 160 |
| C3 | Ca/Zn MVE/MA salt; Na CMC | 4.32 mm | 161 |
| C4 | Ca/Zn MVE/MA salt; Na CMC | 5.31 mm | 142 |
| C5 | Na, CA MVE/MA salt; Na CMC | 6.19 mm | 175 |

The results indicate that commercial products differ substantially in separation stability. Commercial denture adhesive formulations also have a broad range of adhesion profiles, ranging from a short duration (C5), to a longer one with high onset force (C3). These findings correspond to what perceived by most users, i.e., claiming that C5 has a strong hold but a short duration of action while C3 has generally long and strong hold, although it may taste bad because of the presence of Zinc.

The following denture adhesive composition examples were prepared and tested. The table below summarizes the formulations of the examples and the separation stability results after 14 days, where collected and comments on adhesion.

TABLE 3

Example Formulations

| Example ID | Petrolatum 1958 | Petrolatum Sonnercore HV | Mineral Oil | Carbopol 974P | Carbopol 971P | Carbopol 980 | Na CMC 7H3SXF | Gantrez MS-955 | SiO2 | Separation Stability Layer Height | Peak Adhesion Force (N) |
|---|---|---|---|---|---|---|---|---|---|---|---|
| 1 | 14 | 0 | 32 | 25.1 | 0 | 0 | 0 | 0 | 0 | | 135 |
| 2 | 14 | 0 | 32 | 0 | 0 | 0 | 53 | 0 | 0 | | 169 |
| 3 | 14 | 0 | 32 | 0 | 0 | 0 | 0 | 53 | 0 | | 172 |
| 4 | 14 | 0 | 32 | 0 | 12 | 0 | 41 | 0 | 0 | 1.87 | 158 |
| 5 | 14 | 0 | 32 | 0 | 15 | 0 | 38 | 0 | 0 | 3.08 | 159 |
| 6 | 14 | 0 | 32 | 9 | 0 | 0 | 44 | 0 | 0 | | 155 |
| 7 | 14 | 0 | 32 | 12 | 0 | 0 | 41 | 0 | 0 | 2.34 | 173 |
| 8 | 14 | 0 | 32 | 15 | 0 | 0 | 38 | 0 | 0 | 3.59 | 176 |
| 9 | 14 | 0 | 32 | 18 | 0 | 0 | 35 | 0 | 0 | | 142 |
| 10 | 0 | 14 | 32 | 12 | 0 | 0 | 41 | 0 | 0 | | 162 |
| 11 | 0 | 14 | 32 | 12 | 0 | 0 | 41 | 0 | 1 | | 134 |
| 12 | 14 | 0 | 32 | 0 | 0 | 12 | 41 | | | 0.56 | 134 |
| 13 | 14 | 0 | 32 | 0 | 0 | 12 | 38 | | | 2.51 | 141 |

Still more denture adhesive composition examples are prepared and tested. The table below summarizes the formulations of the examples.

TABLE 4

Example Formulations

| Example ID | Petrolatum 1958 | Petrolatum Sonnercore HV | Mineral Oil | Carbopol 974P | Carbopol 971P | Prot. 8223 CR | Na CMC 7H3SXF | Gantrez MS-955 | Poly(ox.) WR-301 | Separation Stability Layer Height | Peak Adhesion Force (N) |
|---|---|---|---|---|---|---|---|---|---|---|---|
| 14 | 14 | 0 | 32 | 15 | 0 | 0 | 24 | 15 | 0 | | 123 |
| 15 | 14 | 0 | 32 | 12 | 0 | 0 | 41 | 0 | 0 | | 172 |
| 16 | 14 | 0 | 32 | 12 | 0 | 0 | 21 | 21 | 0 | | 125 |
| 17 | 14 | 0 | 32 | 12 | 0 | 0 | 0 | 41 | 0 | | 130 |
| 18 | 14 | 0 | 32 | 15 | 0 | 0 | 38 | 0 | 0 | | 176 |
| 19 | 14 | 0 | 32 | 18 | 0 | 0 | 18 | 18 | 0 | | 105 |
| 20 | 14 | 0 | 32 | 18 | 0 | 0 | 36 | 0 | 0 | | 141 |
| 21 | 14 | 0 | 32 | 15 | 0 | 0 | 19.5 | 19.5 | 0 | | 112 |
| 22 | 14 | 0 | 32 | 15 | 0 | 0 | 15 | 24 | 0 | | 114 |
| 23 | 14 | 0 | 32 | 15 | 0 | 0 | 0 | 39 | 0 | | 108 |
| 24 | 14 | 0 | 32 | 18 | 0 | 0 | 0 | 36 | 0 | | 108 |
| 25 | 14 | 0 | 32 | 9 | 0 | 0 | 44 | 0 | 0 | | 155 |
| 26 | 14 | 0 | 32 | 12 | 0 | 0 | 0 | 0 | 41 | | 202 |
| 27 | 14 | 0 | 32 | 12 | 0 | 20.5 | 20.5 | 0 | 0 | | 163 |

Overall, examples using (i) a combination of a cross-linked poly(acrylic) acid polymer, for example Carbopol 974, a carboxymethylcellulose component, for example Na CMC, and a sodium alginate, for example, Protanal 8223 CR; or (ii) a combination of a cross-linked poly(acrylic) acid polymer, for example Carbopol 974, and a poly(ethylene) oxide, for example Poly(ox.) WR-301, showed the best adhesion curve and separation stability performance.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the technology described herein can be used together with ranges or amounts for any of the other elements.

As described hereinafter the molecular weight of the materials described above have been determined using known methods, such as GPC analysis using polystyrene standards. Methods for determining molecular weights of polymers are well known. The methods are described for instance: (i) P. J. Flory, "Principles of star polymer Chemistry", Cornell University Press 91953), Chapter VII, pp 266-315; or (ii) "Macromolecules, an Introduction to star polymer Science", F. A. Bovey and F. H. Winslow, Editors, Academic Press (1979), pp 296-312. As used herein the weight average and number weight average molecular weights of the materials described are obtained by integrating the area under the peak corresponding to the material of interest, excluding peaks associated with diluents, impurities, uncoupled star polymer chains and other additives.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition or method under consideration. That is "consisting essentially of" permits the inclusion of substances that do not materially affect the basic and novel characteristics of the composition under consideration.

While certain representative embodiments and details have been shown for the purpose of illustrating the subject technology described herein, it will be apparent to those skilled in this art that various changes and modifications can be made therein without departing from the scope of the subject invention. In this regard, the scope of the technology described herein is to be limited only by the following claims.

What is claimed is:
1. A denture adhesive composition comprising:
   (a) 10 to 14 percent by weight of the overall composition of a cross-linked poly(acrylic) acid polymer, wherein the cross-linked poly(acrylic) acid polymer is a carbomer homopolymer, carbomer copolymer, carbomer interpolymer, or a mixture thereof; and
   (b) an additional component comprising (i) 17 to 25 percent by weight of the overall composition of a carboxymethylcellulose component; and (ii) 18 to 45 percent by weight of the overall composition of an adherence promoting component comprising sodium alginate;
   wherein the weight ratio of component (b) to component (a) is from 5:1 to 1:5.
2. The denture adhesive composition of claim 1 wherein the carboxymethylcellulose component comprises a sodium carboxymethylcellulose.
3. The denture adhesive composition of claim 1 wherein the carboxymethylcellulose component comprises a carboxymethylcellulose with seven degrees of substitution, a high viscosity grade, a viscosity of about 3000 cps viscosity, a smooth flow property, a fine particle size, and made to at least a food grade standard.

4. The denture adhesive composition of claim 1 wherein the adherence promoting component further comprises poly (ethylene) oxide.

5. The denture adhesive composition of claim 1 wherein the balance of the composition comprises a medium, where said medium comprises a mineral oil, petrolatum, or a mixture thereof.

6. The denture adhesive composition of claim 1 wherein the composition further comprises a medium, where said medium comprises a mineral oil, petrolatum, or a mixture thereof, and wherein the medium is present in an amount from about 14 to about 50 percent by weight.

7. The denture adhesive composition of claim 1;
wherein said cross-linked poly(acrylic) acid polymer of (a) comprises a carbomer homopolymer;
wherein the carboxymethylcellulose component of (b)(i) comprises a sodium carboxymethylcellulose;
wherein the adherence promoting component of (b)(ii) comprises sodium alginate; and
wherein the composition further comprises a mineral oil, petrolatum, or a mixture thereof.

8. The denture adhesive composition of claim 1 wherein the cross-linked poly(acrylic) acid polymer comprises a carbomer homopolymer present in the overall composition at about 10 to about 14 percent by weight;
wherein the carboxymethylcellulose component comprises a sodium carboxymethylcellulose present at about 18 to about 24 percent by weight;
wherein the adherence promoting component comprises sodium alginate and is present at about 18 to about 45 percent by weight;
wherein the composition further comprises a petrolatum present at about 30 to about 34 percent by weight; and
wherein the composition further comprises mineral oil present at about 12 to about 16 percent by weight.

* * * * *